US010226316B2

(12) United States Patent
Ratto

(10) Patent No.: US 10,226,316 B2
(45) Date of Patent: Mar. 12, 2019

(54) METHOD FOR PRODUCING AN ARTIFICIAL ANAL SPHINCTER AND PROSTHESIS THEREOF

(71) Applicant: COLOPROCT RESEARCH S.R.L., Rome (IT)

(72) Inventor: Carlo Ratto, Rome (IT)

(73) Assignee: THD S.P.A., Correggio (IT)

( * ) Notice: Subject to any disclaimer, the term of this patent is extended or adjusted under 35 U.S.C. 154(b) by 780 days.

(21) Appl. No.: 14/818,767

(22) Filed: Aug. 5, 2015

(65) Prior Publication Data

US 2017/0035541 A1 Feb. 9, 2017

(51) Int. Cl.
*A61F 2/00* (2006.01)

(52) U.S. Cl.
CPC .................. *A61F 2/0036* (2013.01)

(58) Field of Classification Search
CPC ........... A61F 2/0036; A61F 2/02; A61F 2/004
USPC .............................................. 600/29, 30, 31
See application file for complete search history.

(56) References Cited

U.S. PATENT DOCUMENTS

| 7,381,180 | B2 | 6/2008 | Gerber et al. | |
|---|---|---|---|---|
| 2003/0153806 | A1* | 8/2003 | Miller | A61F 2/0036 600/30 |
| 2005/0096497 | A1* | 5/2005 | Gerber | A61F 2/0036 600/30 |
| 2006/0257446 | A1* | 11/2006 | Tropsha | A61B 17/12 424/423 |
| 2015/0065790 | A1* | 3/2015 | Silverman | A61B 17/12022 600/30 |
| 2015/0356891 | A1* | 12/2015 | Will | G09B 23/285 434/272 |

\* cited by examiner

*Primary Examiner* — Kaylee R Wilson
(74) *Attorney, Agent, or Firm* — Pearne & Gordon LLP

(57) ABSTRACT

A method for producing an artificial sphincter comprises the steps of effecting a skin incision (2), forming a passage (3) for a prosthesis (4) and releasing the prosthesis (4) inside the passage (3). Said prosthesis passing from one miniaturized state in the step preceding the release, to an expanded state in the step following the release. The steps mentioned above are repeated at least seven times in order to release at least seven prosthesis (4), which are uniformly distributed along a circumferential arc (5) surrounding the anal canal (AC); said at least seven prosthesis (4) defining a plurality of prosthesis (40) forming a third artificial sphincter.

6 Claims, 5 Drawing Sheets

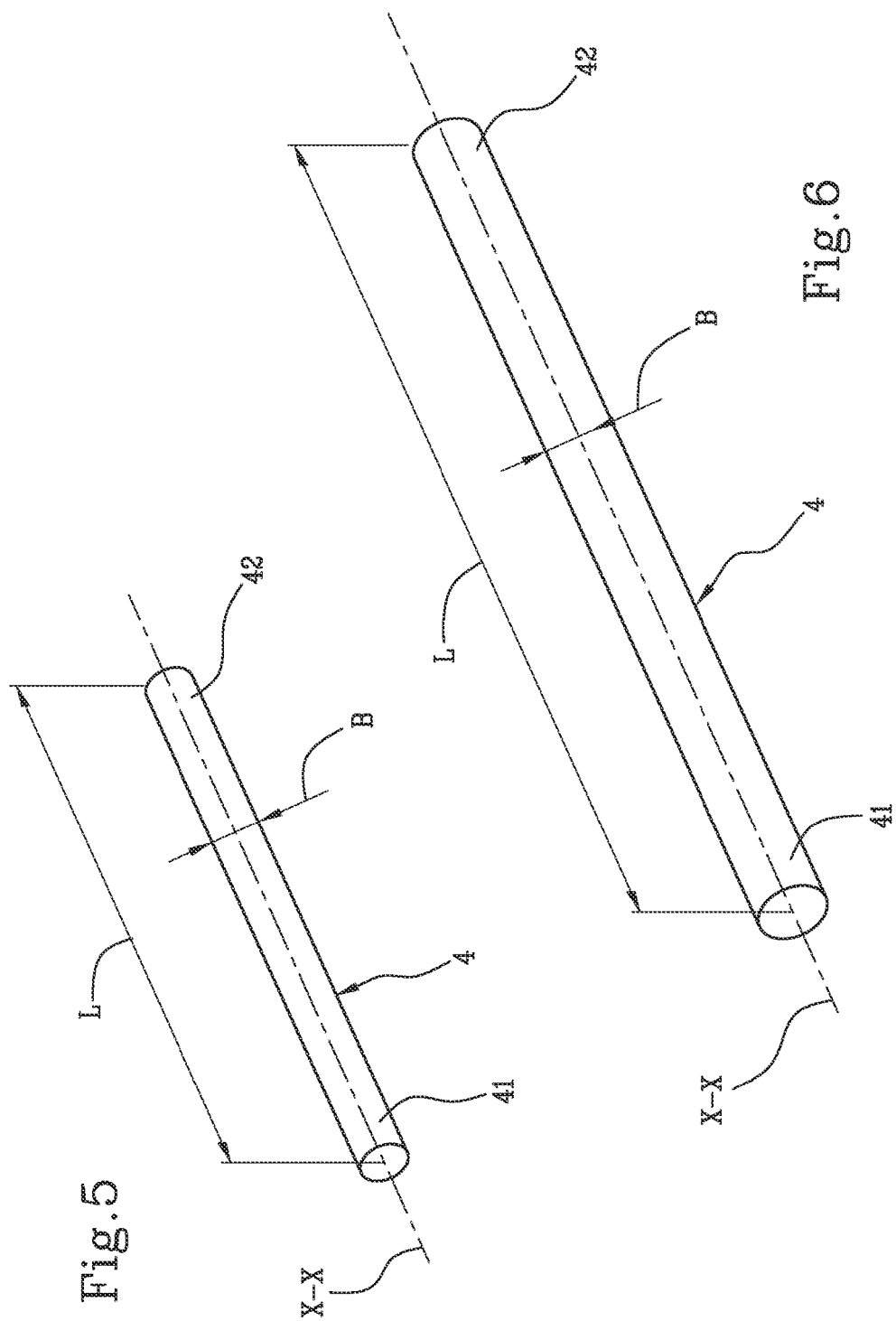

METHOD FOR PRODUCING AN ARTIFICIAL ANAL SPHINCTER AND PROSTHESIS THEREOF

The present invention has for object a method for producing an artificial anal sphincter.

It is a further object of the invention to provide a prosthesis for producing an artificial anal sphincter.

The method and the prosthesis herein disclosed are applicable to the surgical-medical sector, more specifically to the sector of colon-proctology medicine, i.e. that medicine branch which is concerned with all diseases and disorders affecting the last stretch of the digestive tract, that is to say, colon, rectum and anus.

The anal region is constituted by a sophisticated muscle complex generally destined to continence.

The anal sphincter complex consists of two concentric muscle structures: the external sphincter apparatus, and the internal sphincter, between which an intermediate layer of vertical fibers is interposed, called longitudinal complex layer.

The external sphincter apparatus consists of three main units: a subcutaneous unit, being distal to the inferior margin of the internal sphincter; an oval-shaped surface unit, surrounding the internal sphincter for the whole extension thereof; a deep unit, comprising the pubo-rectalis sling, which in turn is part of the ani levator.

When a patient must evacuate, the faeces, once in the rectum, come in contact with the sensitive part of the anal canal which is located in the upper part thereof thus giving rise to a series of reflexes, even of conscious type, owing to which the patient can respectively contract the sphincters if he/she intends to retain the faeces (where the conditions are not appropriate to defecate), or relax the sphincter and allow passage of the faeces (where the condition is appropriate to evacuate). This latter mechanism of a nervous reflected nature), is termed recto-anal inhibitory reflex. After defecation, the sphincters return to the state of equilibrium, wherein they are generally contracted.

Some patients are affected by sphincter laxity, whereby the continence mechanism briefly described above is seriously compromised, which leads to fecal incontinence. Fecal incontinence can manifest in different severity degree and forms; the pathogenesis per se is multifactorial and varied.

This condition may occur due to sphincter laxity and tone loss thereof, or to the presence of sphincter iatrogenic lesions, or meuro-muscle alterations thereof.

Methods are known for the treatment of fecal incontinence by means of blowing agents as described in U.S. Pat. No. 7,381,180.

This method describes the insertion of one or more blowing prosthesis into the anal-sphincter apparatus.

Blowing prostheses, which consist of biocompatible hydrogel, are inserted through a small incision into the perianal skin. When inserted, the prostheses are in a miniaturized state. The contact of the prosthesis with an organic liquid gives rise to a blowing phenomenon with consequent pressure on the anal sphincter tissue, which leads to a more effective faeces containing capacity.

Although use of this technique has resulted in a significant progress in the surgical approach to fecal incontinence, the Applicant has now identified aspects which further improve in a significant manner the methodology and the prostheses within this sector.

In particular the Applicant has experienced how insertion of the prosthesis inside the anal canal, through an incision of the perianal skin, does not allow a durability in time of the beneficial effects related to the blowing prostheses.

It is an object of the present invention to provide a surgical and implant method for specific prosthesis capable of solving the problems of fecal incontinence.

A further object of the present invention is to provide a surgical method and intervention prostheses thereto related, which is able to ensure the patient a high durability in time of the positioning of the prosthesis inserted into the sphincter complex, thus ensuring a constant durability in time of the beneficial effects attainable by use of blowing prostheses.

Further characteristics and advantages of the present invention will become more apparent from the indicative, and therefore non-limiting, description of a preferred but non-exclusive embodiment of a method for producing an artificial anal sphincter and relative prosthesis, as illustrated in the accompanying drawings wherein:

FIG. 5 illustrates a perspective view of a prosthesis in a miniaturized state thereof, adopted in this method;

FIG. 6 shows a perspective view of a prosthesis adopted in the present method in an expanded state thereof after having been in contact with a liquid, preferably an organic liquid.

Referring to the above figures, FIGS. 1-4 particularly illustrate the steps of a surgical intervention for producing an artificial anal sphincter, while FIGS. 5-6 show some details of the prosthesis used in the present method.

Figure 1:
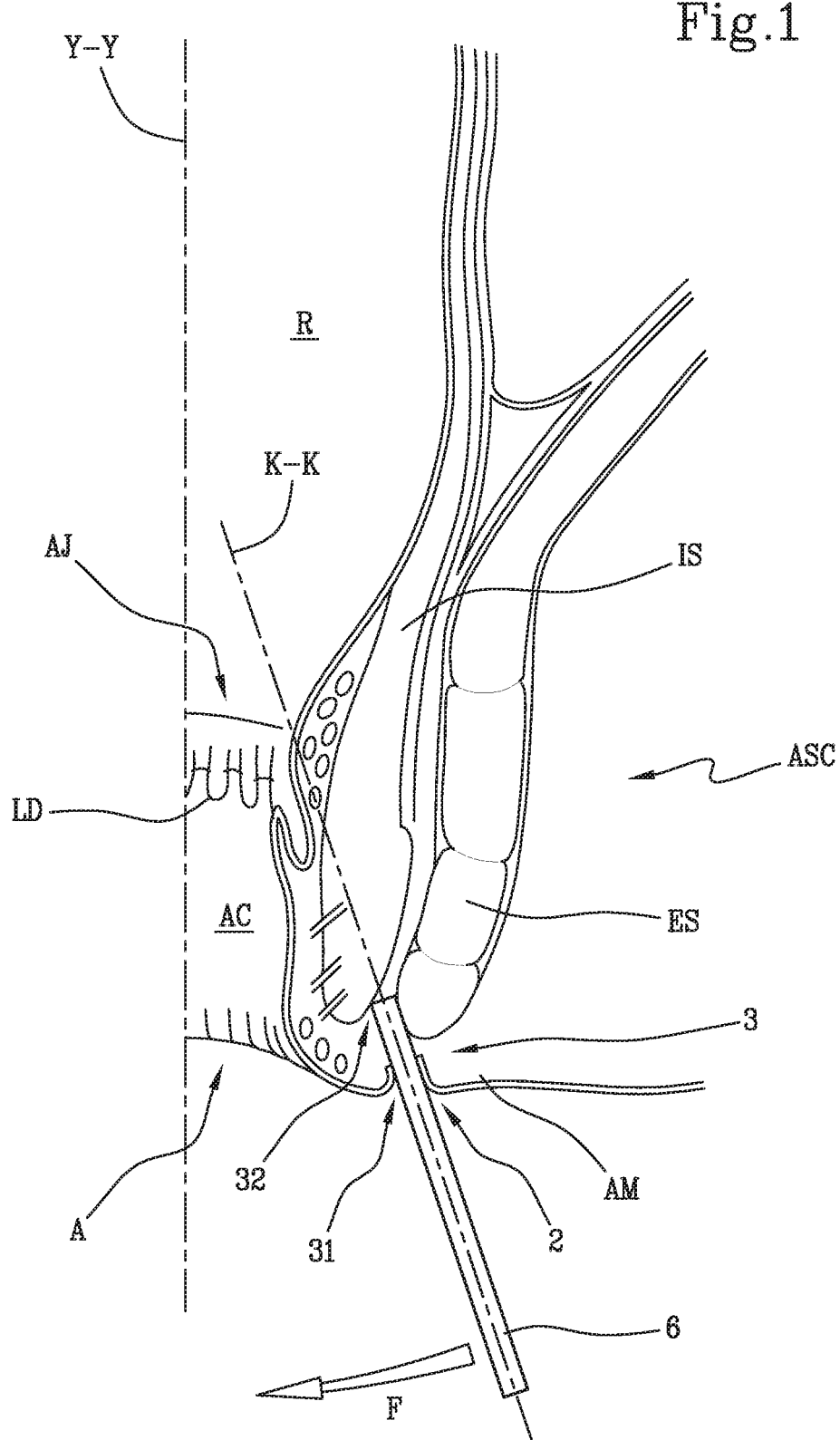
FIG. 1 is a longitudinal sectional view of the anal canal around which a first operating step is performed of the method for producing an artificial sphincter according to the present invention.
Figure 2:
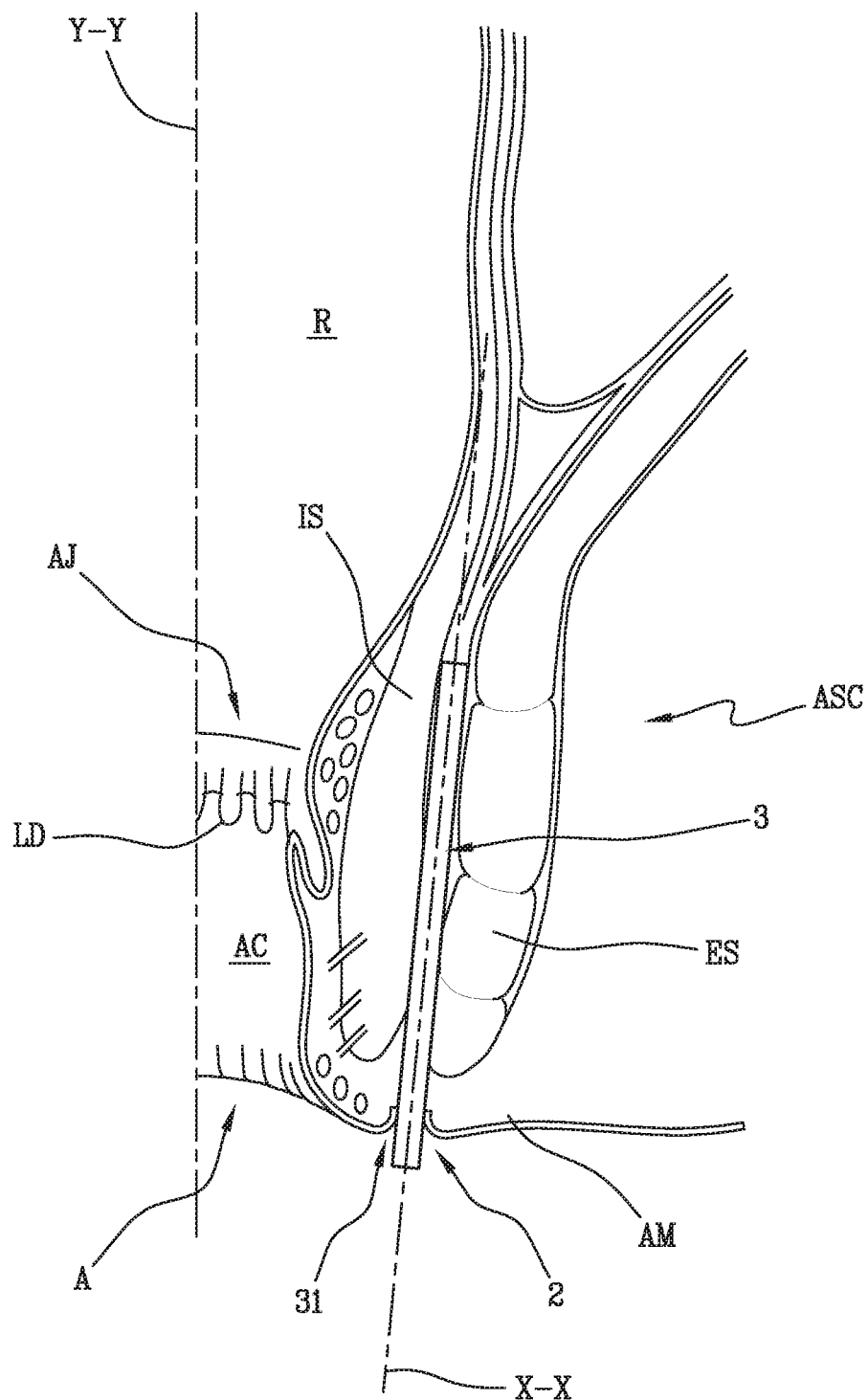
FIG. 2 is a longitudinal sectional view of the anal canal around which an intermediate operating step is performed of the method for producing an artificial sphincter according to the present invention.
Figure 3:
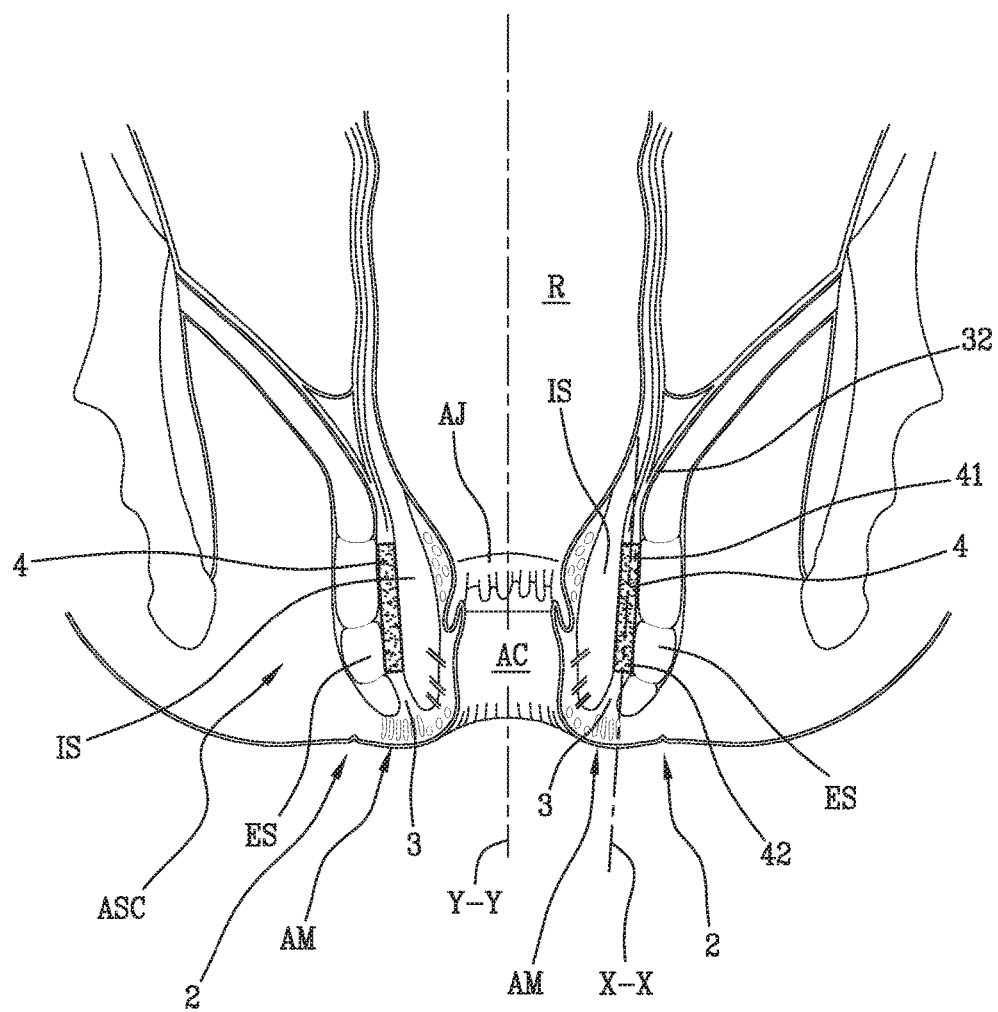
FIG. 3 is a view in longitudinal section of the anal canal around which a final step is performed of the method for producing an artificial sphincter according to the present invention.
Figure 4:
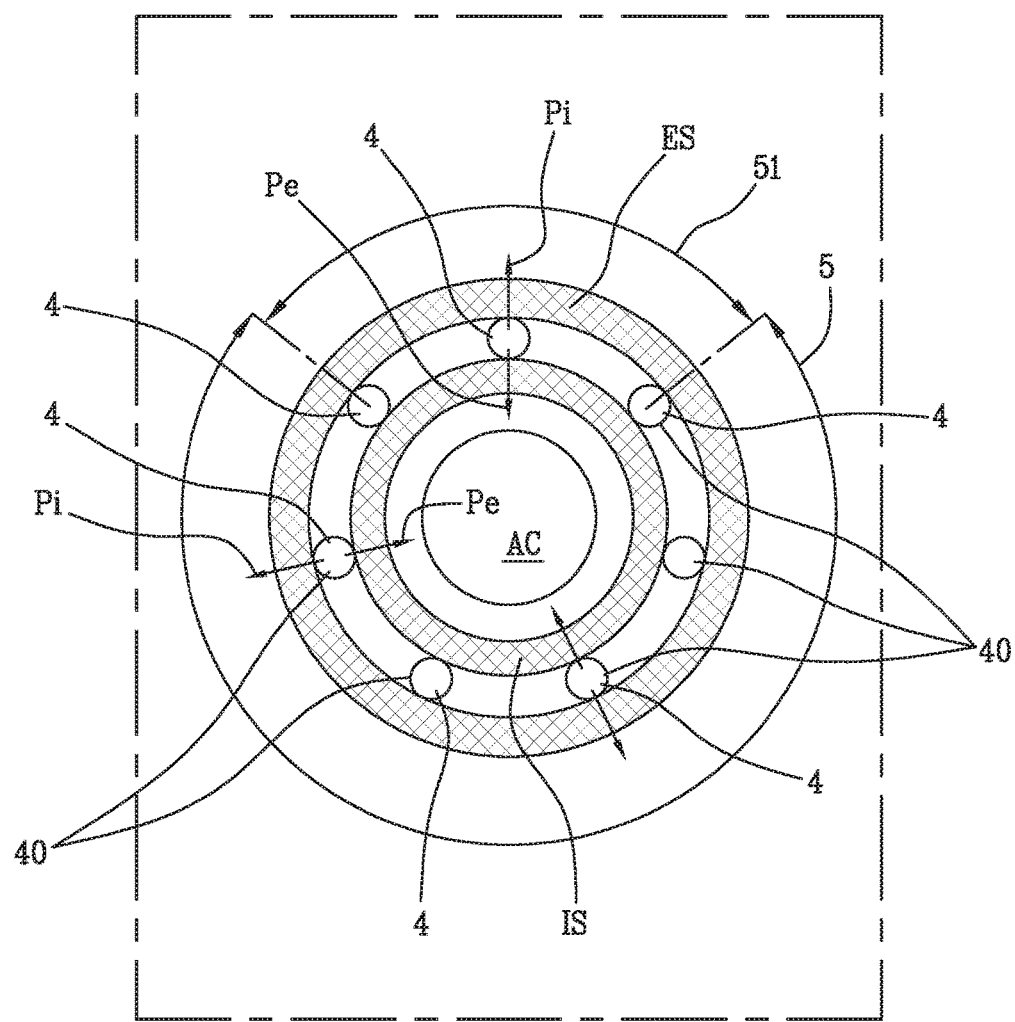
FIG. 4 is a schematic view in cross section of the anal canal of a patient with an artificial sphincter, which is object of the method herein.

In FIG. 1 there is illustrated a vertical section of the anal canal AC. Said anal canal AC exhibits a development axis Y-Y preferably lying in a vertical plane as illustrated in the Figures. Beyond the anorectal junction AJ, said anal cavity AC ends superiorly in the rectum R, and inferiorly, outside the anus A with the skin of the anal margin AM.

The anal canal is surrounded by the anal sphincter complex ASC. The anal sphincter complex is defined by two concentric muscle structures: the internal sphincter IS and the external sphincter ES.

The internal sphincter IS is substantially concentric to the anal canal AC and located next to it, whereas the external sphincter is substantially concentric to the anal canal and located next to the internal sphincter IS.

The method for producing an artificial sphincter provides the steps of:

effecting a second skin incision in proximity of the anal margin AM;

creating a passage 3 which extends from a first open distal end 31, located relative to the incision 2, to a second closed proximal end 33, located externally of the anal canal AC, at the anorectal junction AJ;

releasing a substantially cylindrical-shaped prosthesis 4 with development axis X-X inside the passage 3; said prosthesis passing from a miniaturized state occurring in the step preceding the release, to an expanded state occurring in the step following the release;

wherein the steps listed above are repeated at least seven times in order to release at least seven prosthesis 4 which are uniformly distributed along at least a circumferential arc 5 surrounding the anal canal AC; said at least seven prosthesis 4 defining a plurality of prosthesis 40 forming a third artificial anal sphincter.

Based on surgical trials, the Applicant came to produce an optimal number of prosthesis, comprised between seven and twelve.

More specifically, depending on the morphology of the anal sphincter complex ASC of the patient and/or his/her sphincter laxity degree, the Applicant has determined a number of prosthesis between seven to twelve.

Said plurality of prosthesis is distributed on a circumferential arc 5 which may be open or closed. This distribution is substantially uniform along the circumference 5. Said circumference provides a center lying along the axis Y-Y of the anal cavity AC and a radius between 1.5 and 3 cm.

In other words, the entire circumference 5.51 or the circumferential arc 5, is lying on an ideal plane which is perpendicular to the axis Y-Y and passes transversely through the anal canal AC.

With particular reference to the prosthesis release step, the same occurs within the inter-sphincteric space defined between the internal sphincter IS and the external sphincter ES.

In other words, the Applicant has experienced that the longitudinal complex layer, which is anatomically intermediate between the internal sphincter IS and the external sphincter ES, corresponds to the ideal zone for the release of a plurality of prosthesis 40.

From a geometrical point of view, the inter-sphincteric space assumes a tubular shape with the entire diameter equal to the outer diameter of the internal sphincter, and the external diameter equal to the internal diameter of the external sphincter.

Referring now to a plurality of prosthesis 40, each prosthesis is arranged with the axis X-X thereof parallel to the axis Y-Y of the anal canal AC and internally of the inter-sphincteric space, i.e. inside the tubular volume previously described.

Said plurality of prosthesis 40 is then disposed at a height along the development axis Y-Y of the anal canal AC, which height develops superiorly at the anal junction AJ, and inferiorly below the dentate line DL. Referring to the prosthesis 4, whereby a first proximal end 41 and a second distal end 42 are respectively defined therein, the release step provides that the prosthesis 4 is arranged by positioning the first proximal end 41 thereof, at the height of the anus rectal junction AJ.

In order to facilitate the release step of the prosthesis 4, a cannula 6 is used. More precisely, the prosthesis 4 is made to slide inside the cannula 6 in order to be positioned within the inter-sphincteric space. This cannula 6 is also used for favouring formation of the passage 3.

With particular reference to the forming of the passage 3, this is achieved on the base of the following sub-steps:
  inserting a sensing element inside the anal cavity AC, preferably a surgeon's finger;
  penetrating the first open distal end 31 by means of the cannula 6;
  moving the cannula along a direction K-K transverse to the axis Y-Y of the anal canal AC, up to detecting the presence of the cannula 6 in proximity of the anal canal AC via the sensing element;
  rotating the cannula 6 so as to bring it to the axis Y-Y of the anal canal AC with parallel orientation;
  pushing the cannula 6 along a direction parallel to the axis Y-Y of the anal canal AC, until the anal rectal junction is reached.

The surgeon's finger, or more generally the sensing element, is aimed at preventing any perforation of the anal canal AC.

In fact, as soon as the cannula 6, which is inserted into the open distal end 31, starts pushing slightly onto the anal canal, the movement thereof along the direction K-K is made to stop.

Here, a connection point 32 between the open distal end 31 and the closed proximal end 33, is determined.

In other words, the connection point 32 is determined by the intersection between the first movement direction K-K of the cannula 6 and the direction parallel to the axis Y-Y of the anal canal AC.

Rotation of the cannula 6 occurs relative to the connection point 32, wherein said cannula 6 is positioned with an orientation parallel to the axis Y-Y of the anal canal AC.

Said rotation is illustrated in FIG. 1 by the arrow F, wherein the cannula 6 is rotating thereby coming closer to the anal canal AC.

With particular reference to the incision step 2, the Applicant has determined as the optimum distance that comprised between 0.5 cm and 3 cm from the anal margin AM.

In this manner, the second proximal distal end 42 of the released prosthesis 4 does not lie in proximity of the incision 2.

From a geometrical point of view, by extending ideally the axis X-X of the prosthesis 4, defined by the straight line passing the first proximal end 41 and the second distal end 42, this extension does not intersect the first open distal end 31 of the passage 3.

This means that the second distal end 42 is not in line with the first open distal end 31 of the passage 3.

In this way, not even a minimal settlement or movement of the prosthesis 4 inside the passage 3 will cause it to exit therefrom.

The plurality of prosthesis 40 therefore forms a third anal sphincter defined by an annular artificial crown predisposed for generating an external pressure on the internal sphincter and an internal pressure on the external sphincter.

In other words, the plurality of prosthesis 40 generates an external pressure on the internal sphincter IS, and an inner pressure on the external sphincter ES.

The plurality of prosthesis 40 then facilitates relaxing of the muscle bundles of the internal sphincter from outside, and of the muscle bundles of the external sphincter from inside, thereby favouring the contractible ability of the sphincters.

In FIG. 5 there is illustrated a prosthesis 4 preferably exhibiting a substantially elongated cylindrical shape. This prosthesis is illustrated in a miniaturized version or even in an anhydrous state.

FIG. 6 illustrates a preferably cylindrical-shaped prosthesis 4 in the expanded version or even in the hydrate state thereof.

Said prosthesis 4 has a prevalent development along an axis X-X and provides a length L and a principal transverse dimension B.

The length L is in the range between 15 mm and 35 mm, preferably 25 mm.

Said main transverse dimension B is in the range between 1.7 mm and 4.3 mm, preferably 3 mm.

Where the shape is a cylindrical shape, the main transverse dimension B is defined by the diameter, whereas in case of a parallelepiped shape, the main transverse dimension B is defined by the side.

When passing from the anhydrous to the hydrated state, between 1:6 and 1:10 preferably 1:8, the prosthesis exhibits a ratio between the volumes.

During the transition from the anhydrous state to the hydrate state, the prosthesis 4 provides an increase in size of the main transverse dimension B and a decrease in size of the length.

As indicated in the method herein disclosed, when in contact with body fluids, the miniaturized status of said prosthesis 4 becomes an expanded status.

The invention claimed is:

1. A method for producing an artificial sphincter in support of an anal sphincter complex defined by an internal sphincter and an external sphincter, both surrounding an anal canal, the internal sphincter extending along an axis of the anal canal, and ending superiorly in a rectum through an anorectal junction, and inferiorly outside an anus with skin of an anal margin, said method comprising the following steps:
   effecting a skin incision in proximity of the anal margin;
   creating a passage extending from a first open distal end defined by the incision, to a second closed proximal end located externally of the anal canal at the anorectal junction;
   releasing a substantially cylindrical-shaped prosthesis with a development axis inside the passage; said prosthesis passing from a miniaturized state preceding the release to an expanded state following the release;
   wherein the steps listed above are repeated at least seven times in order to release at least seven prostheses which are uniformly distributed along a circumference surrounding the anal canal; said at least seven prostheses defining a plurality of prostheses forming an artificial sphincter, wherein said plurality of prostheses are uniformly distributed along a circumference with a center thereof in the axis of the anal canal and a radius between 1.5 and 3 cm, wherein the development axis of each prosthesis is distant from the center by a distance equal to the radius; and
   wherein said step of releasing the prosthesis occurs inside an inter-sphincteric space defined between the internal sphincter and the external sphincter.

2. A method according to claim 1, wherein each prosthesis has a first proximal end and a second distal end; and said releasing step occurs by displacing the first proximal end of the prosthesis at a height of the anorectal junction.

3. A method according to claim 1, wherein said releasing step occurs by means of a cannula, the cannula adapted to form the passage via the skin incision, the prosthesis is adapted to slide inside the cannula to be positioned within the inter-sphincteric space.

4. A method according to claim 3, wherein said incision step occurs at a distance between 0.5 and 3 cm from the anal margin.

5. A method according to claim 1, wherein an extension of the development axis does not pass through the first open distal end of the passage.

6. A method according to claim 1, wherein said plurality of prostheses generates an external pressure on the internal sphincter and an internal pressure on the external sphincter.

* * * * *